United States Patent [19]

Anderson et al.

[11] Patent Number: 5,651,862

[45] Date of Patent: Jul. 29, 1997

[54] WET-FORMED ABSORBENT COMPOSITE

[75] Inventors: Richard Allen Anderson; Richard John Schmidt, both of Roswell, Ga.

[73] Assignee: Kimberly-Clark Worldwide, Inc.

[21] Appl. No.: 744,137

[22] Filed: Aug. 13, 1991

[51] Int. Cl.⁶ .................................................. D21H 21/22
[52] U.S. Cl. .................. 162/127; 162/146; 162/168.1; 162/175; 162/177; 162/183
[58] Field of Search ........................ 162/123, 127, 162/168.1, 157.6, 112, 183, 146, 100, 125, 175, 111, 177

[56] References Cited

U.S. PATENT DOCUMENTS

| | | | |
|---|---|---|---|
| 3,419,345 | 12/1968 | Parrish | 8/137.5 |
| 3,420,734 | 1/1969 | Anderson et al. | 162/135 |
| 3,431,166 | 3/1969 | Mizutani et al. | 162/135 |
| 3,551,410 | 12/1970 | MacDonald et al. | 260/212 |
| 3,686,024 | 8/1972 | Nankee et al. | 117/140 A |
| 3,826,711 | 7/1974 | Schoggen et al. | 162/102 |
| 3,998,690 | 12/1976 | Lyness et al. | 162/141 |
| 4,117,184 | 9/1978 | Erickson et al. | 428/224 |
| 4,250,306 | 2/1981 | Lask et al. | 536/88 |
| 4,256,877 | 3/1981 | Karlsson et al. | 536/59 |
| 4,260,443 | 4/1981 | Lindsay et al. | 156/220 |
| 4,344,818 | 8/1982 | Nuttal et al. | 162/111 |
| 4,354,901 | 10/1982 | Kopolow | 162/158 |
| 4,486,268 | 12/1984 | Nuttall et al. | 162/123 |
| 4,500,585 | 2/1985 | Erickson | 428/152 |
| 4,551,142 | 11/1985 | Kopolow | 604/368 |
| 4,552,618 | 11/1985 | Kopolow | 162/157.6 |
| 4,710,270 | 12/1987 | Sunden et al. | 162/175 |
| 4,851,069 | 7/1989 | Packard et al. | 156/284 |
| 4,986,882 | 1/1991 | Mackey et al. | 162/123 |
| 5,049,235 | 9/1991 | Barcus et al. | 162/157.6 |
| 5,102,501 | 4/1992 | Eber et al. | 162/112 |

FOREIGN PATENT DOCUMENTS

| | | |
|---|---|---|
| 0212618A1 | 3/1987 | European Pat. Off. . |
| 0359615 | 3/1990 | European Pat. Off. . |
| 0408128A2 | 1/1991 | European Pat. Off. . |
| 0437816 | 7/1991 | European Pat. Off. . |
| 2468320 | 5/1981 | France . |
| WO84/4315 | 11/1984 | WIPO . |
| WO91/09916 | 7/1991 | WIPO . |

*Primary Examiner*—Peter Chin
*Attorney, Agent, or Firm*—Jeffrey B. Curtin; Thomas J. Mielke

[57] ABSTRACT

Described is a wet-formed composite. The wet-formed composite is formed from a combination of fibers and absorbent material. Specifically, the wet-formed composite is formed from absorbent material and a fiber slurry wherein the absorbent material is swellable in the dispersion medium of the slurry. Also disclosed is a method of forming the wet-formed composite. The method involves forming a fiber slurry, combining an absorbent material with the fiber slurry prior to forming the composite and then forming and drying the composite. The absorbent material is swellable in the dispersion medium of the fiber slurry.

10 Claims, 8 Drawing Sheets

5,651,862

WET-FORMED ABSORBENT COMPOSITE

BACKGROUND OF THE INVENTION

1. Field of the Invention

The present invention relates to a wet-formed composite. Specifically, the present invention relates to a wet-formed absorbent composite comprising an absorbent material and fibers.

2. Description of the Related Art

Absorbent composites suitable for use in absorbent products such as diapers, feminine care products, adult incontinence products, wound dressings, training pants, wipes, mats and the like are known. As a general rule, the absorbent composites comprise an absorbent matrix of fibers. Such a fiber matrix tends to have a relatively low specific absorption capacity. Accordingly, absorbent products needing a relatively high absorbent capacity and employing such a fiber matrix tend to be relatively thick and bulky. In an attempt to increase the absorbent capacity of the fiber matrix, absorbent materials, known in the art as superabsorbents, have been introduced into the fiber matrix. As a general rule, the fiber of the matrix and the absorbent material are intermixed in an air stream and deposited on a porous forming surface to form a relatively lofty mixture of absorbent material and fiber. Such mixtures are known in the art as air-laid, or air-formed structures.

In an attempt to produce thinner absorbent composites and products, more absorbent material has been added to the air-laid fiber matrix. Unfortunately, the porous nature of the air-laid fiber matrix may prevent it from containing relatively high amounts of absorbent material.

As an alternative to air-laid absorbent composites formed from fibers and absorbent material, it has been proposed to form absorbent composites from wet-laid fibrous structures such as tissue, in conjunction with absorbent material. For example, U.S. Pat. No. 3,686,024 issued Aug. 22, 1972, to Nankee et al. describes a process of making a water-absorbent coated article and the resulting product. Described is a fibrous support on which a water-swellable, substantially water-insoluble polymer gel, substantially swollen with water, is impressed.

Similarly, U.S. Pat. No. 4,260,443 issued Apr. 7, 1981, to Lindsay et al. is directed to a laminated absorbent process. Disclosed is a process in which a dry, liquid-absorbing material is applied to a first sheet. A second water-permeable sheet is superimposed on the first sheet. Water is applied at spaced points to the second sheet to moisten the liquid-absorbing material and cause it to serve as an adhesive, bonding the first and second sheets together.

U.S. Pat. No. 4,851,069 issued Jul. 25, 1989, to Packard et al. is directed to a process for making tissue-absorbent particle laminates. According to the described process, a moistening liquid is applied to a first tissue layer. The moistened surface of the first tissue is showered with dry absorbent particles, which particles are of a nature to be rendered adhesive by absorption of the moistening liquid. A second tissue is superposed on the first tissue, and the tissues bonded together by passing through a nip between heated rollers.

European Patent Application 0 359 615 published Mar. 21, 1990, is directed to the manufacture of superabsorbent composite structures. Described is a method wherein a water-laid web of cellulosic fibers is formed. A dry, solid absorbent is applied directly to the web prior to drying of the web and a pre-formed web is laid over the absorbent. The resultant laminated web is then dried.

As a general rule, the products and processes described above involve forming a laminate of an absorbent material with one or two pre-formed layers of fiber material. Such laminated structures have been found to be quite useful. Unfortunately, it is sometimes difficult to effectively contain large quantities of absorbent material between the two layers of fiber material. Additionally, when relatively large quantities of absorbent material are present between the two layers, the laminates tend to delaminate. The problem of delamination is particularly noticed when the laminates are wetted.

As an alternative, U.S. Pat. No. 4,986,882 issued Jan. 22, 1991, to Mackey et al. describes an absorbent paper comprising a polymer-modified fibrous pulp and a wet-laying process for the production thereof. Described are wet-laid paper sheets formed from two or more fibrous cellulosic pulps. One of the pulps is a polymer-modified pulp capable of being protonated and which, in its alkali-metal-cation exchange state, imbibes water by hydrocolloidal swelling. The second pulp is a non-polymer modified cellulosic pulp. The absorbent paper sheet is made such that the first pulp is wet laid in a protonated state such that it tends not to swell. The wet-laid web is then brought to the alkali-metal-cation exchange state and dried.

Those processes involving a substantial pre-swelling of the absorbent material tend to be costly due to the difficulty associated with removing water from such absorbent materials.

It is desired to provide an absorbent composite and a method for making the absorbent composite which are improved when compared to the prior art.

SUMMARY OF THE INVENTION

The present invention concerns, in a first aspect, a wet-formed composite. The wet-formed composite comprises a combination of fibers and absorbent material. The wet-formed composite is formed from a combination of absorbent material and a slurry comprising the fibers dispersed in a dispersion medium. In one embodiment, the absorbent material is swellable in the dispersion medium.

In a second aspect, the present invention concerns a method for the manufacture of a wet-formed composite. The method involves forming a slurry from fibers and a dispersion medium, from which slurry a wet-formed composite can be made. An absorbent material, which may be swellable in the dispersion medium, is then combined with the fiber slurry prior to forming the wet-formed composite. The wet-formed composite containing a combination of fibers and absorbent material is then formed by removing at least some of the dispersion medium.

DETAILED DESCRIPTION OF THE PREFERRED EMBODIMENT

Figure 1:
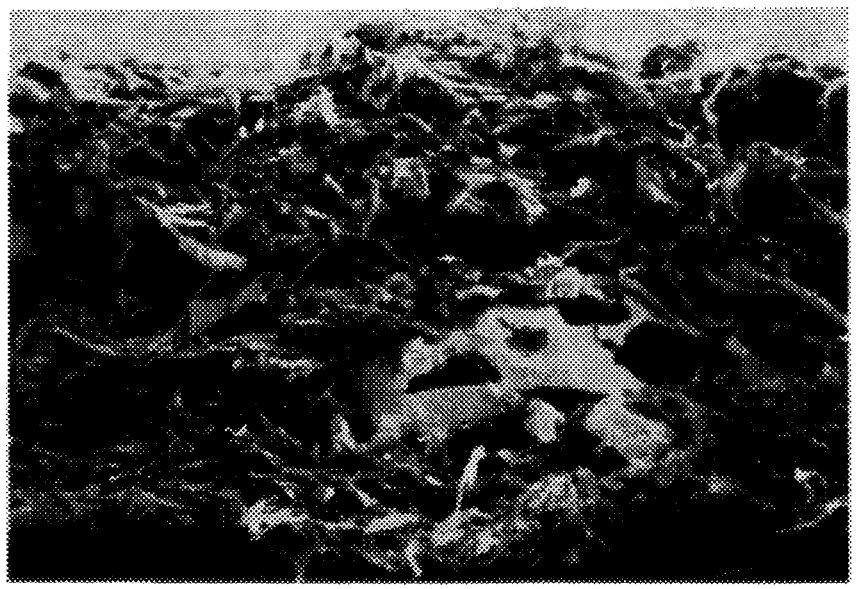
FIG. 1 is a scanning electron photomicrograph of a wet-formed composite according to the present invention.

The present invention relates, in one aspect, to a wet-formed composite. The wet-formed composite comprises a combination of fibers and absorbent material. The wet-formed composite is formed from a combination of absorbent material and a slurry comprising fibers dispersed in a dispersion medium. The absorbent material is desirably swellable in the dispersion medium.

Fibers suitable for use in the present invention are known to those skilled in the art. Any fiber from which a wet-formed composite can be formed is believed suitable for use. Examples of fibers suitable for use in the present invention include, cellulosic fibers such as wood pulp, cotton linters, cotton fibers and the like; synthetic polymeric fibers such as polyolefin fibers, polyamide fibers, polyester fibers, polyvinyl alcohol fibers, polyvinyl acetate fibers, synthetic polyolefin wood pulp fibers, and the like; as well as regenerated cellulose fibers such as rayon and cellulose acetate microfibers. Mixtures of various fiber types are also suitable for use. For example, a mixture of cellulosic fibers and synthetic polymeric fibers may be used. As a general rule, the fibers will have a length-to-diameter ratio of at least about 2:1, preferably of at least about 5:1. As used herein, "diameter" refers to a true diameter if generally circular fibers are used or to a maximum transverse cross-sectional dimension if non-circular, e.g., ribbon-like, fibers are used. The fibers will generally have a length of from about 0.5 millimeter to about 25 millimeters, preferably from about 1 millimeter to about 6 millimeters. Fiber diameters will generally be from about 0.001 millimeter to about 1.0 millimeter, preferably from about 0.005 millimeter to about 0.01 millimeter. For reasons such as economy, availability, physical properties, and ease of handling, cellulosic wood pulp fibers are preferred for use in the present invention.

As used herein, the term "absorbent material", "absorbent", and similar terms refer to a water-swellable, generally water-insoluble material capable of absorbing at least about 5, desirably about 20, and preferably about 100 times or more its weight in water. The absorbent material may be formed from organic material which may include natural materials such as agar, pectin, and guar gum, as well as synthetic materials such as synthetic hydrogel polymers. Synthetic hydrogel polymers include, for example, carboxymethylcellulose, alkali metal salts of polyacrylic acid, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water-insoluble. Crosslinking may, for example, be by irradiation or by covalent, ionic, Van der Waals, or hydrogen bonding. Suitable materials are available from various commercial vendors, such as the Dow Chemical Company, Cellanese Corporation, Allied-Colloid Inc., and Stockhausen Inc. The noncellulosic, synthetic hydrogel polymers are preferred for use in the present invention.

The absorbent material may be in the form of discrete particles, agglomerated particles, fibers, spheres or the like. When in the form of discrete particles, the particles will generally have a maximum cross-sectional dimension of from about 10 micrometers to about 2000 micrometers, preferably of from about 50 micrometers to about 1000 micrometers.

As used herein, the terms "wet-formed,""wet-laid,"0 and the like refer to composites which are formed from a process in which fibers are dispersed in a liquid dispersion medium to form a slurry. The slurry is deposited on a forming surface to form the composite by removal of at least a portion of the dispersion medium. Those skilled in the art are familiar with such processes.

The absorbent material present in the wet-formed composites is suitably swellable in the dispersion medium. As used herein, an absorbent material will be considered to be swellable in the dispersion medium when the absorbent material can absorb at least five times, preferably at least twenty times, and most preferably at least one hundred times or more its weight in the dispersion medium when the absorbent material is dispersed in an excess of the dispersion medium for a period of one hour.

The wet-formed composites of the present invention comprise an absorbent material. The absorbent material of the present invention is combined with the fibers, desirably with the slurry comprising the fibers prior to formation of the wet-formed composite. Preferably, the absorbent material is combined with the fiber slurry immediately prior to formation of the wet-formed composite. Specifically, it is desired that the absorbent materials be combined with the slurry of fibers such that the absorbent material absorbs less than about 10 times its weight in the dispersion medium, desirably less than about 5 times its weight in the dispersion medium, preferably less than about 3 times its weight in the dispersion medium, and most preferably, less than about 1.5 times its weight in the dispersion medium.

The maximum amount of dispersion medium which the absorbent material absorbs, after being combined with the slurry of fibers and dispersion medium until the point of drying, can be determined by comparing the weight of the wet composite, prior to drying, to the weight of the dry composite after drying. The weight of dispersion medium removed by drying generally represents the maximum amount of dispersion medium capable of being absorbed by the absorbent material. Such a calculation assumes all dispersion medium removed by drying was present in the absorbent material. The actual amount of dispersion medium held in the absorbent material prior to drying is less than the calculated maximum amount and depends on the length of exposure of the absorbent material to the dispersion medium, as well as the relative amounts of fiber and absorbent material in the wet-formed composites.

A variety of materials may be suitable for use as the dispersion medium. Exemplary of suitable dispersion mediums are water, other aqueous materials, and the like. For reasons such as availability and economy, water is the preferred dispersion medium.

The fibers are suitably present in the dispersion medium in an amount of from about 0.005 to about 3.0 weight percent, preferably of from about 0.01 to about 2.0 weight percent and, most preferably, of from about 0.01 to about 1.0 weight percent, based on total weight of the fibers and dispersion medium. The dispersion medium may contain other additives known to those skilled in the art of papermaking. Other suitable additives include, without limitation, binders, viscosity modifiers, adhesives, wet-strength additives, pH control additives, flocculants, and the like, provided they do not deleteriously affect the formation or performance properties of the wet-formed composites.

The dried wet-formed composites of the present invention comprise fibers in an amount of from about 5 to about 95, desirably of from about 5 to about 65, preferably of from about 5 to about 40, and, most preferably, of from about 10 to about 30 weight percent based on total weight of the fibers and absorbent material present in the wet-formed composite. The absorbent material is present in an amount of from about 5 to 95, desirably of from about 35 to about 95, preferably of from about 60 to about 95 and, most preferably, of from about 70 to about 90 weight percent based on total weight of the fibers and absorbent material present in the wet-formed composite.

Applicants have observed that, at higher concentrations of absorbent material, the composites are less stiff (softer). It is hypothesized that this results from a lower degree of fiber-to-fiber hydrogen bonding due to the large concentration of absorbent material and the associated lower degree of fiber-fiber contact. Of course, at higher concentrations of absorbent material, bonding between the absorbent material particles and between the absorbent material particles and the fibers may increase.

The wet-formed composites of the present invention generally have a basis weight of from about 20 to about 1000, preferably of from about 50 to about 200 and, most preferably, of from about 100 to about 200 grams per square meter. A wide variety of basis weights are possible. Lower basis weights are often preferred due to the relative ease of dewatering and drying the low basis weight composites at high manufacturing speeds. If manufacturing speed is not a concern, higher basis weight composites can be formed. It is desirable to dewater the wet-formed composites immediately after formation to avoid substantial absorption of the dispersion medium by the absorbent material. At higher basis weights, dewatering of the composites in a rapid manner becomes more difficult and the absorbent material has more time in which to absorb the dispersion medium. The more dispersion medium absorbed by the absorbent material, the less efficient the drying process.

The wet-formed composites of the present invention generally have a density of from about 0.05 to about 0.75, preferably of from about 0.05 to about 0.5 and, most preferably, of from about 0.05 to about 0.25 grams per cubic centimeter. Density is calculated according to the following formula: density (g/cc): basis weight (gsm)/[thickness (millimeters)×10001]. For the purposes of this application, thicknesses are determined by physical measurement through the use of a 3 inch platten under a load of about 0.2 pounds per square inch. Applicants have found that physical thickness measurements, such as that described above, tend to be greater than optical measurements, such as that obtained through the use of a scanning electron photomicrograph. Applicants hypothesize that this difference may result from small irregularities in the composite surface possibly resulting from the presence of the particles of absorbent material.

Applicants have found that by combining the absorbent material and fiber slurry prior to formation of the wet-formed composite, a composite possessing improved performance properties can be produced. Specifically, Applicants have found that substantial containment of the absorbent material is achieved even at relatively high concentrations of the absorbent material relative to the concentration of fiber. Prior art structures consisting of laminates, wherein absorbent material is sandwiched between two pre-formed layers of fiber sheets, are generally good at containing relatively low concentrations of absorbent material. At higher concentrations of absorbent material, the laminates tend to leak absorbent material in part because the laminates tend to delaminate. This is particularly true at cut or slit edges. When the laminates are employed in absorbent products such as diapers, absorbent material which leaks from the laminate can end up contacting the body of a wearer. This is undesirable.

Without intending to be bound hereby, Applicants hypothesize that the improved performance properties achievable with the wet-formed composites of the present invention are due to a greater degree of mixing between the fibers and the absorbent material compared to laminate structures. This greater degree of mixing is achieved through the process of combining the fiber slurry and absorbent material prior to formation of the wet-formed composite.

FIG. 1 is a scanning electron photomicrograph of a cross section of a wet-formed composite according to the present invention. As can be seen from reference to FIG. 1, the absorbent material present in the wet-formed composite is in intimate contact with the fibers. Moreover, the fibers are seen to extend generally throughout the entire thickness of the wet-formed composite.

Figure 2:
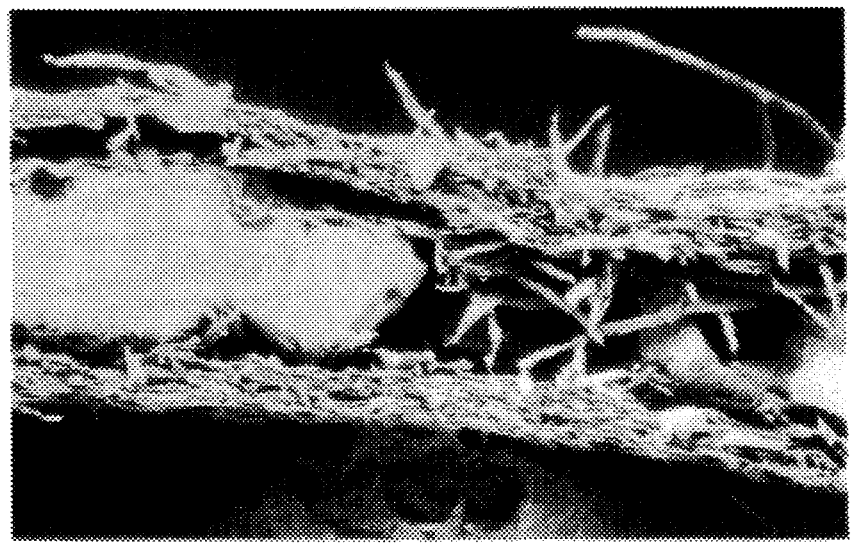
FIG. 2 is a scanning electron photomicrograph of a first laminated absorbent composite according to the prior art.
Figure 3:
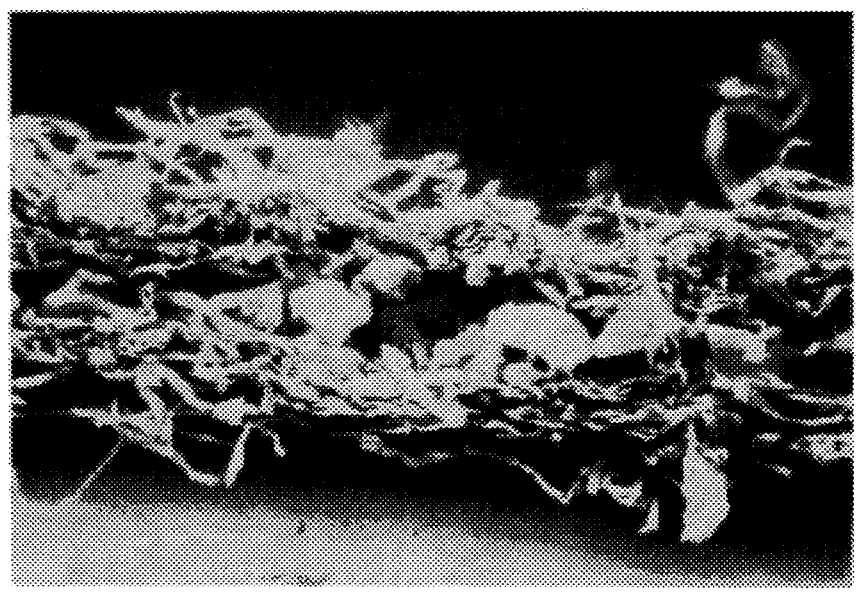
FIG. 3 is a scanning electron photomicrograph of a second laminated absorbent composite according to the prior art.

FIGS. 2 and 3 illustrate scanning electron photomicrographs of prior art laminates. As can be seen from reference to FIGS. 2 and 3, there is much less mixing and, therefore, less contact between the fibers of the tissue sheet and the absorbent material. Additionally, fibers are not necessarily present throughout the thickness of the laminate.

Applicants hypothesize that the greater degree of mixing between the fibers and the absorbent material allows for improved fluid transfer into and throughout the thickness of the wet-formed composite. This, in turn, may allow the absorbent material to function more efficiently by providing additional contact between the absorbent material and liquid present in the composite.

As will be discussed in greater detail below, depending on the process used to form the wet-formed composites of the present invention, various positioning of the absorbent material relative to the fibers present in the wet-formed composite can be achieved. This allows production of composite having different absorbent behavior. This aspect of the present invention can best be understood by reference to the figures, wherein like numerals refer to like materials.

Figure 4:
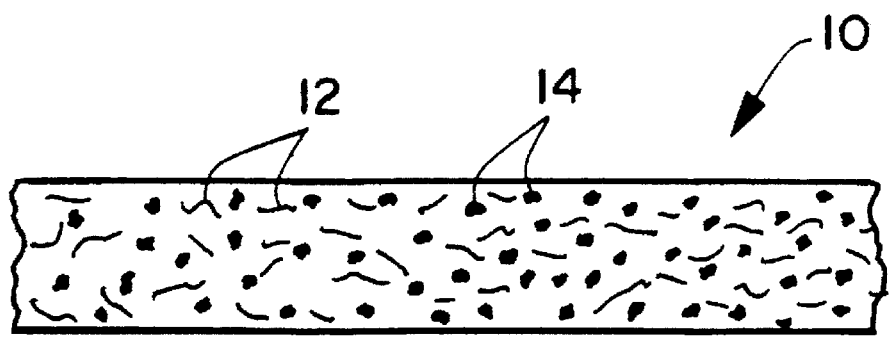
FIG. 4 illustrates a cross-sectional view of a wet-formed composite according to a first embodiment of the present invention.

FIG. 4 illustrates a cross-sectional view of a first embodiment of the present invention. In FIG. 4, a wet-formed composite 10 is illustrated. The wet-formed composite comprises fibers 12 in which individual particles of absorbent material 14 are distributed. As can be seen from reference to FIG. 4, the particles of absorbent material are generally uniformly distributed with the fibers. This generally uniform distribution of the absorbent material and fibers occurs when a relatively high degree of mixing of absorbent material and fiber occurs prior to formation of the wet-formed composite.

Figure 5:
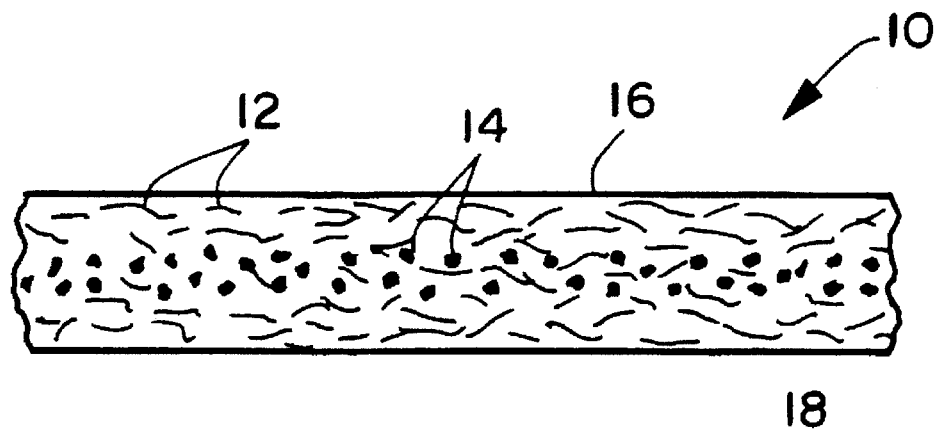
FIG. 5 illustrates a cross-sectional view of a wet-formed composite according to a second embodiment of the present invention.

An alternative relative positioning is shown in FIG. 5 wherein a second wet-formed composite is illustrated. As can be seen from reference to FIG. 5, the particles of absorbent material 14 are not uniformly distributed but are preferentially zoned throughout the thickness of the composite 10. Specifically, the particles of absorbent material 14 are relatively highly concentrated (zoned) in the center of the wet-formed composite 10. The fibers 12 are more highly concentrated on the outer surfaces 16, 18 of the wet-formed composite 10. At least 55 weight percent, preferably at least 60 weight percent and, most preferably, at least 70 weight percent of the absorbent material present in the wet-formed composite is located in the central half of the thickness of the wet-formed composite 10. That is, if the thickness of the wet-formed composite is determined and divided into equal quarters, the middle two quarters contain at least 55 weight percent of the absorbent material; while the first quarter and fourth quarter, each of which contain an outer surface of the wet-formed composite, contain the remainder of the absorbent material.

Methods of determining the amount of absorbent material present in the various quarters of the thickness of the composite are known to those skilled in the art. Such methods include chemical methods or optical methods, such as image analysis, and the like.

Figure 6:
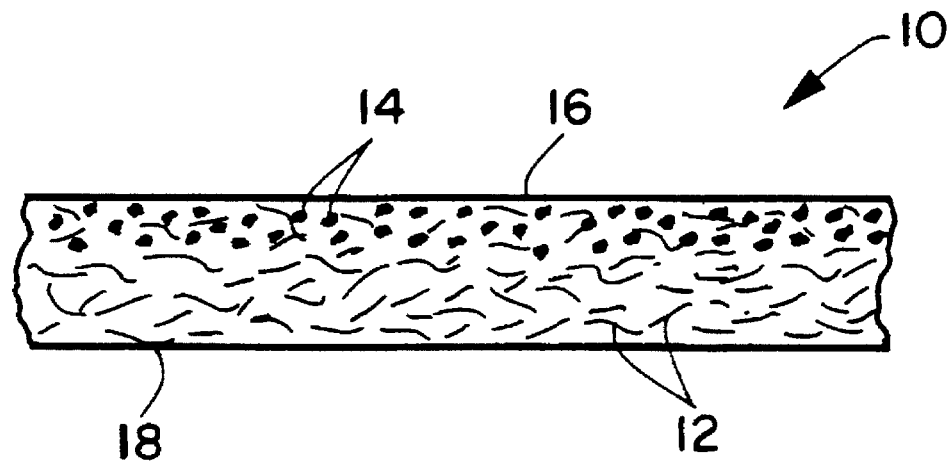
FIG. 6 illustrates a cross-sectional view of a wet-formed composite according to a third embodiment of the present invention.

FIG. 6 illustrates a third alternative relative positioning of the absorbent material and fibers present in the wet-formed composite 10. As can be seen from reference to FIG. 6, a majority of the particles of absorbent material 14 is zoned or concentrated at one outer surface 16 of the absorbent composite 10. The opposite outer surface 18 contains a higher concentration of fibers 12. Other possible arrangements of absorbent material and fiber will be apparent to those skilled in the art.

Applicants believe, without intending to be bound thereby, that the ability of the wet-formed composites of the present invention to substantially contain the absorbent material results from the wet-forming process. It is believed that, if the absorbent material has a relatively high gel strength and is allowed to swell to a relatively low degree during the wet-forming process, little or substantially no bonding may occur between the absorbent particles and the fibers. Nonetheless, the wet-formed composites of cellulosic fibers exhibit a relatively high degree of interfiber hydrogen bonding, such that the fibers are substantially bonded to one another. Thus, the absorbent material is contained due to the bonding between the fibers. As the absorbent material is allowed to swell to a greater degree during formation of the wet-formed composite, it is believed that the surface of the absorbent material may become more tacky, thus allowing additional bonding between the absorbent material and the fibers. Similarly, use of absorbent materials having a lower gel strength may lead to bonding between the absorbent material and fibers. Both methods of bonding allow the absorbent material to be substantially contained within the wet-formed composites.

When fibers which do not form hydrogen bonds are employed, e.g., polyolefin fibers, containment of the absorbent material results entirely from bonding between the absorbent material and fiber. If additional bonding is desired, it may be possible to use adhesive binders and the like.

It is desired that the composites of the present invention contain the absorbent material. Specifically, it is desired that the composites have a shake out value of less than about 10 percent, desirably of less than about 2 percent, preferably, of less than about 0.5 percent and, most preferably, of less than about 0.2 percent as determined as set forth below in connection with the examples.

In a second aspect, the present invention concerns a method for the manufacture of a wet-formed composite. The steps of the method comprise forming a slurry of fibers and a dispersion medium, from which slurry a wet-formed composite can be made. An absorbent material, which may be swellable in the dispersion medium, is then combined with the fiber slurry prior to forming the wet-formed composite. A wet-formed composite containing a combination of fibrous material and absorbent material is then formed and dried. Components such as fiber, dispersion medium, and absorbent material suitable for use in the described method are the same as set forth above.

Figure 7:
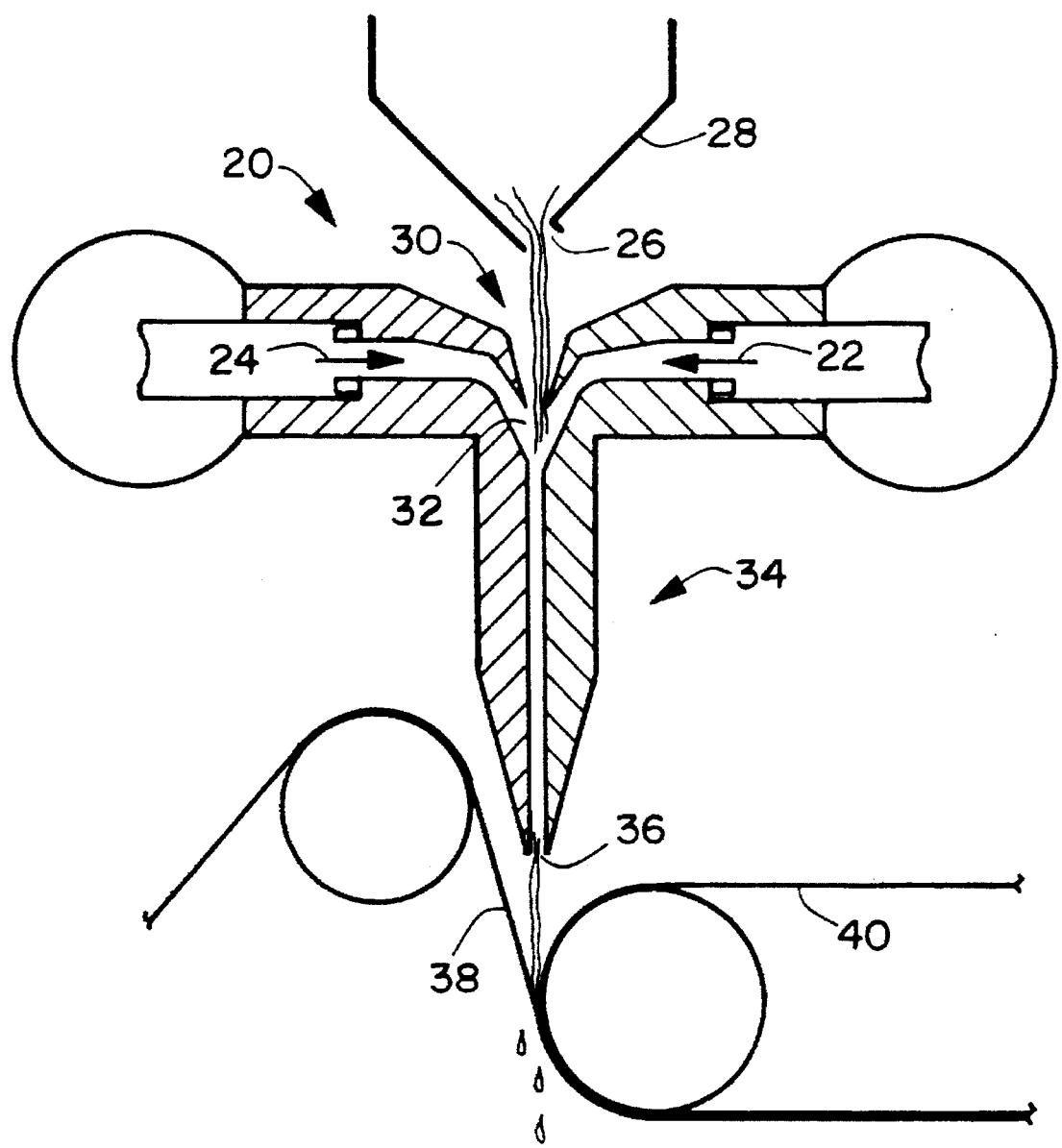
FIG. 7 illustrates a cross-sectional view of a first apparatus suitable for use in the present invention.
Figure 8:
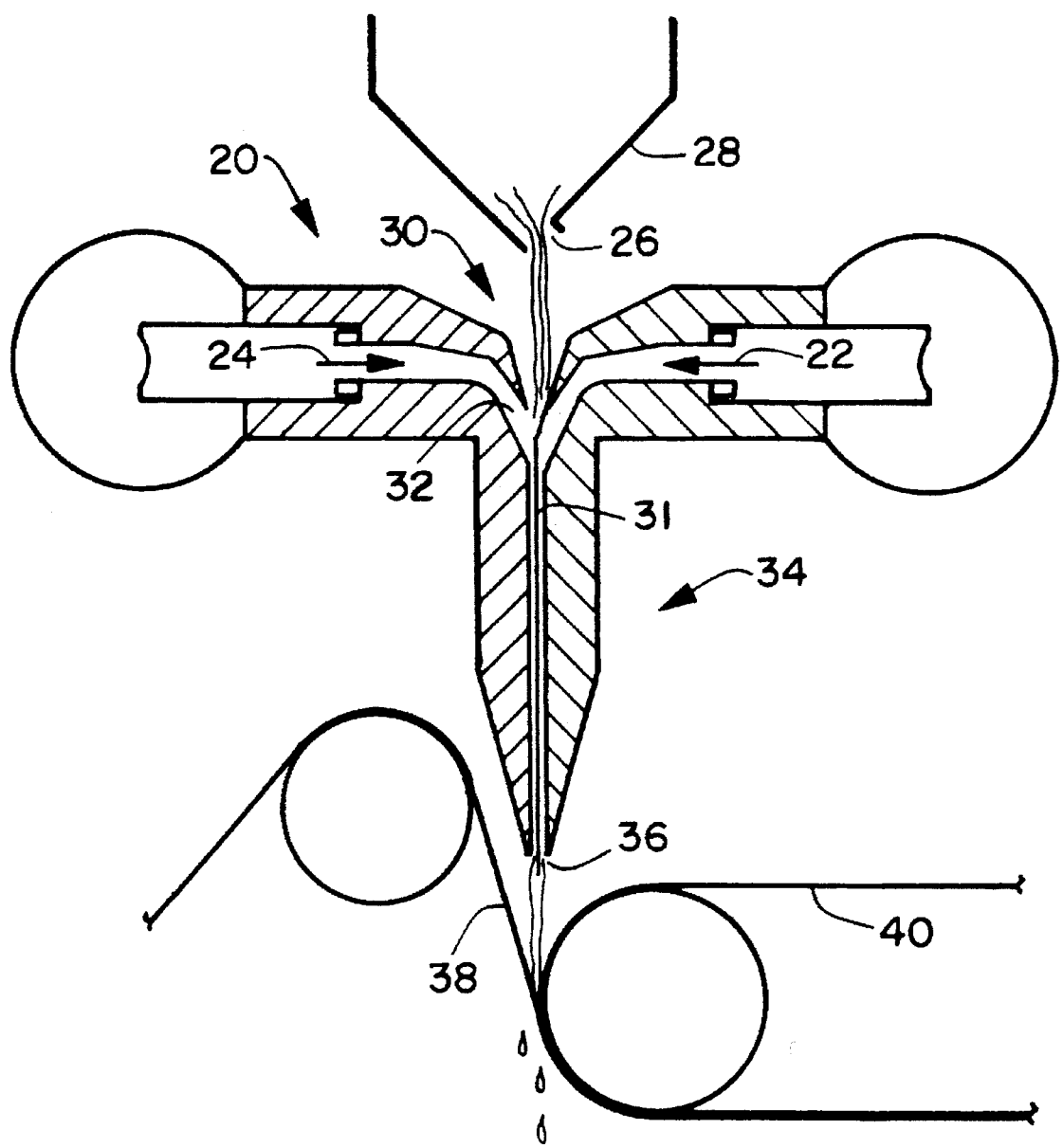
FIG. 8 illustrates a cross-sectional view of a second apparatus suitable for use in the present invention.
Figure 9:
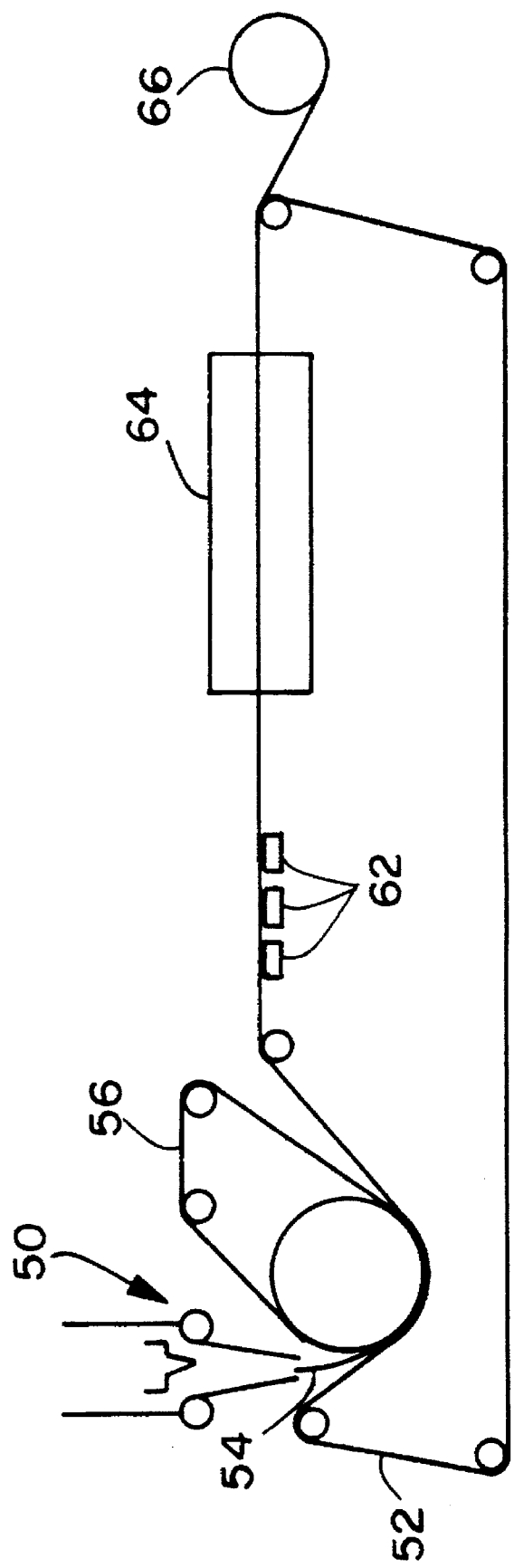
FIG. 9 is a schematic illustration of an apparatus suitable for forming the wet-formed composites and practicing the method of the present invention.

The method of the present invention can best be understood by reference to FIGS. 7–9. FIG. 7 illustrates one apparatus suitable for use in the present invention. The apparatus comprises a multiple flow channeled headbox 20. Multiple flow, channeled headboxes are known to those skilled in the art. One such design is described in U.S. Pat. No. 4,486,268 issued Dec. 4, 1984, to Nuttall et al. Typically, such headboxes are employed to form multi-layer, wet-formed structures. The headbox of FIG. 7 is adapted to combine three material flows. Specifically, a first feedstock, such as a fiber slurry, is provided through opening 22. A second feedstock, such as a fiber slurry, is provided through opening 24. Means of preparing and providing feedstocks, such as fiber slurries, are known to those skilled in the art and are not illustrated. A third feedstock, such as particulate absorbent material 26 is provided from supply means 28. The absorbent material 26 is desirably provided in a dry form and may beneficially be contained in an air stream to minimize contact with water. The third feedstock may comprise material such as fillers, extenders, wet end additives, and the like, in addition to absorbent material.

As used herein, absorbent material will be considered to be dry when it contains less than about 25 percent, and preferably less than about 10 percent moisture. As can be seen from reference to FIG. 7, the third feedstock comprising absorbent material 26 is supplied to headbox 20 through opening 30 generally at the intersection of the fiber slurries entering through openings 22, 24. Mixing of the fiber slurries and absorbent material occurs generally in area 32 and in nozzle 34. The mixture of fiber slurry and absorbent material passes through nozzle 34, exiting through opening 36 and is deposited between forming wires 38 and 40, wherein drainage of the dispersion medium occurs. Additional dispersion medium is extracted from the composite through the application of pressure, vacuum or both. Those skilled in the art will recognize that the method described in connection with FIG. 7 is a twin wire forming process and will appreciate that a single wire process could be used.

Opening 30 may be open to the ambient atmosphere. The feedstocks entering area 32 from openings 22, 24 are generally under pressure. Accordingly, it is desired to size the opening through which the feedstocks enter area 32 relative to the opening present in nozzle 34 and opening 36 such that forces are created at opening 30 to pull the absorbent material into area 32.

Figure 10:
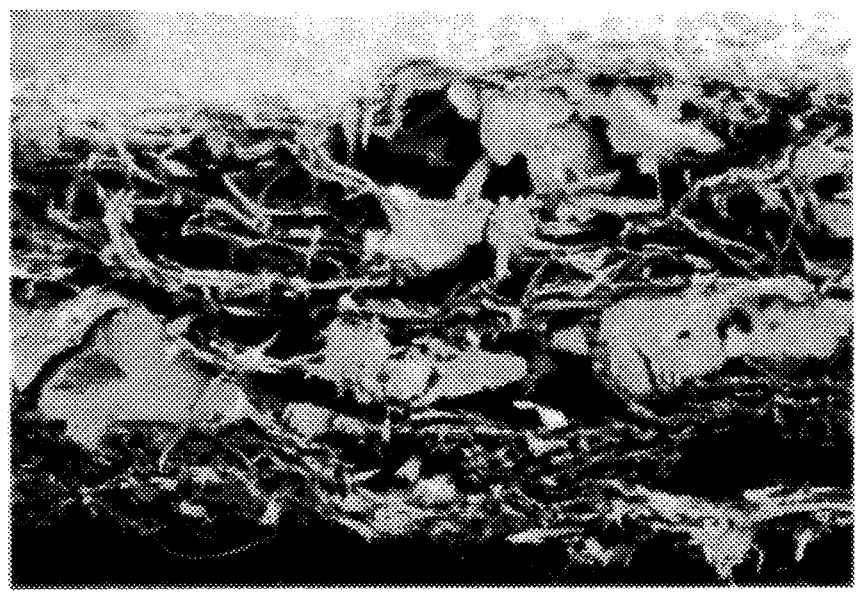
FIG. 10 is a scanning electron photomicrograph of a cross-section of the wet-formed composite of Example 1.

The apparatus illustrated in FIG. 7 is suitably used to form wet-formed composites having a generally uniform distribution of absorbent material and fibers, such as that illustrated in FIGS. 1, 4, or 10. A generally uniform distribution, such as that illustrated in FIG. 4, is best achieved by obtaining a high degree of mixing in area 32 and nozzle 34.

The first and second feedstocks may comprise the same materials or may comprise different materials. For example, when the feedstocks comprise fiber slurries, the first and second fiber slurries may comprise identical mixtures of fiber and dispersion medium or may comprise different fibers or different mixtures of fibers and dispersion medium. In some instances it may be advantageous to employ fibers having different properties such as fiber type, fiber length, fiber diameter, etc. in forming the two fiber slurries. As a result, the feedstocks may have different fluid properties. In this manner, a wet-formed composite having one type of fiber on one outer surface and a different type of fiber on the opposite outer surface can be formed. For example, one surface may comprise fibers selected to maximize wicking of liquids, while the opposite surface may comprise fibers selected to maximize capacity.

FIG. 8 illustrates a forming apparatus similar to that illustrated in FIG. 7. Specifically, openings 22 and 24 are provided to receive a feedstock. Particles of absorbent material 26 are provided from means 28 through opening 30 into area 32. The apparatus of FIG. 8 differs from that of FIG. 7 in that a divider 31 is located in area 32 and nozzle 34, whereby mixing of the feedstock entering through opening 22 with the feedstocks entering through openings 24 and 30 does not occur until the feedstocks have exited nozzle 34 at opening 36. Mixing between the absorbent particles 26 and the feedstock entering through opening 24 occurs in area 32 in a manner similar to that described in connection with FIG. 7. The feedstock materials exit nozzle 34 through opening 36 and are deposited between forming wires 38 and 40, wherein drainage of the dispersion medium occurs. Additional dispersion medium is extracted from the composite through the application of pressure, vacuum, or both.

The presence of divider 31 prevents a high degree of mixing between the feedstock entering through opening 22 and the feedstocks entering through openings 24 and 30. An apparatus, such as that illustrated in FIG. 8, allows for the production of a wet-formed composite, such as those illustrated in FIGS. 5 and 6. Specifically, the fibers entering through opening 22 undergo very little mixing with the absorbent material particles prior to deposition on forming wire 38. A relatively high degree of mixing can occur between the feedstock entering through opening 24 and opening 30. In this manner, the absorbent material can be concentrated in the central region or at one outer surface of the wet-formed composite.

Figure 11:
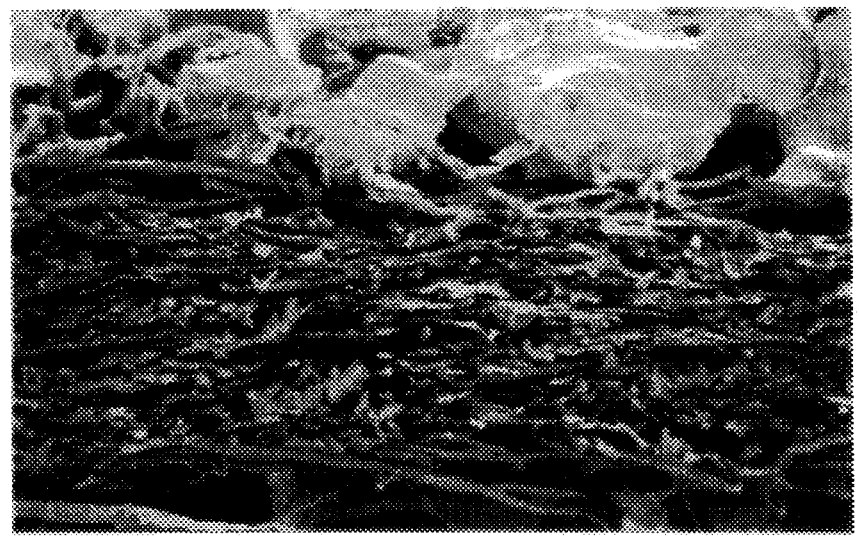
FIG. 11 is a scanning electron photomicrograph of a cross-section of the wet-formed composite of Example 2.

In some instances, where a high concentration of absorbent material is desired at one outer surface of the wet-formed composite, as shown in FIGS. 6 and 11, the feedstock entering through opening 24 may comprise water or other dispersion medium with a lower concentration of fiber than that present in the feedstock entering through opening 22 or, in fact, the feedstock entering through opening 24 may comprise, for example, water alone. Still further, a composite can be formed even when no material is entering through opening 22.

Figure 12:
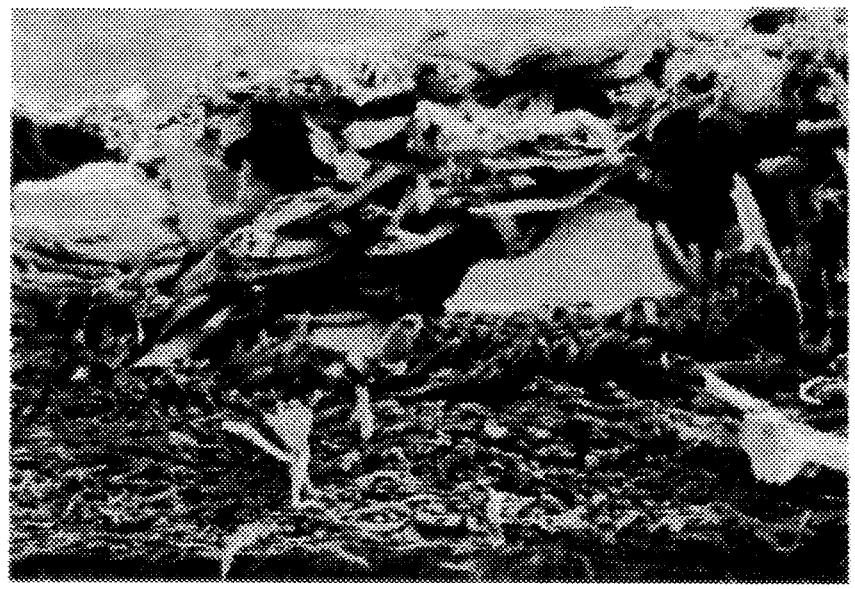
FIG. 12 is a scanning electron photomicrograph of a cross-section of the wet-formed composite of Example 3.

When a high concentration of absorbent material is desired in the central region, as shown in FIGS. 5 and 12, the feedstock entering through opening 24 comprises fibers. The feedstocks entering through openings 22, 24 may contain different concentrations and types of fibers. Other arrangements of fiber and absorbent material can be formed by controlling other formation variables.

FIG. 9 is a schematic illustration of the method according to the present invention. According to the method illustrated in FIG. 9, a combination of absorbent material and a fiber slurry is deposited from a headbox 50 between forming wires 52 and 56. It is understood that headbox 50 may comprise a headbox such as those illustrated in FIGS. 7 and 8 or other suitable design. Wet-formed composite 54 then passes over vacuum chamber 62 at which time dispersion medium is removed from the wet-formed composite 54. The wet-formed composite 54 then passes through drying means 64, for removing the desired amount of the remaining dispersion medium to obtain a wet-formed composite having the desired dryness. Wet-formed composite 54 is then wound about uptake roll 66 or may be creped and then wound.

Those skilled in the art will recognize suitable means for use as the vacuum chamber 62. Additionally, those skilled in the art will recognize that drying means 64 may comprise any of a wide variety of dryers known for use in the papermaking art. Exemplary of such dryers are Yankee dryers, through-air dryers, infrared dryers, microwave dryers, and the like. As a general rule, it is desired that wet-formed composites be dried to a moisture content within the range of from about 0 to about 25, preferably of from about 5 to about 15 weight percent based on total composite weight.

The wet-formed composites of the present invention are suitably employed in absorbent products such as diapers, training pants, feminine care products, adult incontinent garments, and the like. When the composites are employed in diapers, the composites are suitably sandwiched between a liquid-pervious bodyside liner and a liquid-impervious outer cover. In one preferred use, the wet-formed composites of the present inventions are employed as a flushable absorbent insert in a disposable diaper.

Test Methods

Shake Out Test

A test sample about 2.5 inches×11 inches is provided and weighed. The sample to be tested is mounted on a lint-free blotter stock or card stock having dimensions of 3 inches×12 inches. The sample to be tested is mounted to the blotter stock by placing the sample to be tested in the center of a 6 inch×15 inch piece of 0.4 ounce per square yard spunbond material, such as that typically used as bodyside liners for disposable diapers. The blotter stock is placed on top of and covers the sample to be tested and the spunbond material wrapped around and adhered to the surface of the blotter stock opposite the sample to be tested. The spunbond material is porous, such that the individual fibers and particles of absorbent material, from which the sample to be tested is formed, can pass through the spunbond material. The sample to be tested is then placed in an RX-24 shaker commercially available from Tyler Co. and shaken for a period of five minutes. The shaker is modified to hold a basket in which the test sample can be located. Debris falling from the sample to be tested is collected into filter cassettes and weighed. The reported shakeout value is calculated by dividing the weight of the debris falling from the sample being tested by the weight of the absorbent material present in the sample tested and is reported as a percent of the weight of the absorbent material present in the sample to be tested. It is assumed, for the purpose of this test, that all of the material falling from the sample being tested is absorbent material. This assumption is consistent with the observed debris.

EXAMPLE 1

A wet-formed composite according to the present invention is prepared utilizing the apparatus illustrated in FIGS. 7 and 9. The first feedstock is a slurry of water and wood pulp fibers, said slurry having a consistency of 1.75 percent. As used herein, the consistency of a slurry is defined as the weight percent of the wood pulp fibers present in the slurry, based on the total weight of the slurry. The wood pulp fibers used are a softwood bleached chemithermo mechanical pulp commercially available from Cascades, Inc. under the trade designation Black Spruce 601/80. The second feedstock is an aqueous slurry of eucalyptus wood pulp said slurry having a consistency of 2.0 percent. The eucalyptus wood pulp is commercially available from Aracruz Cellulose. The absorbent material is a polyacrylate based absorbent commercially available from Hoechst-Celanese Corporation under the trade designation IM-5000P. The absorbent particles have a particle size of from about 90 to about 600 micrometers. A wet-formed composite is formed and dried to a moisture content of about 0 to 10 weight percent based on total composite weight. The wet-formed composite comprises 21 weight percent bleached chemithermo mechanical pulp, 27 weight percent eucalyptus pulp and 52 weight percent absorbent material, based on the total weight of the bone dry wet-formed composite. The composite has a basis weight of 327 grams per square meter and a density of 0.19 grams per cubic centimeter. A cross sectional scanning electron photomicrograph of the wet-formed composite thus formed appears as FIG. 10.

EXAMPLE 2

A wet-formed composite according to the present invention is formed using the apparatus illustrated in FIGS. 8 and 9. The first feedstock is the aqueous slurry described as the second feedstock of Example 1. The second feedstock is water. The absorbent material is the same absorbent material employed in Example 1. A wet-formed composite is formed and dried to a moisture content of about 0 to 10 weight percent, based on total weight of the composite. The wet-formed composite comprises 63 weight percent eucalyptus fibers, and about 37 weight percent absorbent material, based on total weight of the bone dry composite. The composite has a basis weight of 222 grams per square meter and a density of 0.19 grams per cubic centimeter. FIG. 11 is a scanning electron photomicrograph of a cross section of this wet-formed composite.

EXAMPLE 3

A wet-formed composite according to the present invention is formed employing the apparatus illustrated in FIGS. 8 and 9. The first feedstock is the aqueous slurry described as the second feedstock in Example 1. The second feedstock is the aqueous slurry described as the first feedstock in Example 1. The absorbent material is the same as that employed in Example 1. The wet-formed composite according to the present invention is formed and dried to a moisture content of about 0 to 10 weight percent based on total composite weight. The wet-formed composite comprises about 21 weight percent bleached chemithermo mechanical pulp, about 27 weight percent eucalyptus pulp, and about 52 weight percent absorbent material, based on total weight of the bone dry wet-formed composite. The composite has a basis weight of 325 grams per square meter and a density of 0.2 grams per cubic centimeter. A cross sectional scanning electron photomicrograph of the wet-formed composite of this Example appears as FIG. 12.

EXAMPLE 4

A wet-formed composite according to the present invention is formed using the apparatus illustrated in FIGS. 8 and 9. The first feedstock comprises a slurry of water and bleached softwood (southern pine) pulp. The slurry has a consistency of 0.5 percent. The second feedstock is the same as the first feedstock. The absorbent material is the same as that employed in Example 1. A composite according to the present invention is formed and dried to a moisture content of about 0 to 10 weight percent base on total composite weight. The absorbent composite comprises about 24 weight percent bleached softwood fibers and about 76 weight percent absorbent material. The wet-formed composite of this example is found to have an average shakeout value of about 0.02 percent, a basis weight of 145 grams per square meter and a density of 0.25 grams per cubic centimeter.

EXAMPLE 5

A wet-formed composite according to the present invention is formed as set forth in Example 4. The composite is then mechanically softened by embossing between patterned steel rolls. The softened composite is found to have an average shakeout value of about 0.02 percent, a basis weight of 145 grams per square meter and a density of 0.15 grams per cubic centimeter.

EXAMPLE 6

A wet-formed composite according to the present invention is formed as set forth in Example 4, except the feedstocks are varied to produce a wet-formed composite comprising about 50 weight percent softwood fiber and about 50 weight percent absorbent material based on the total weight of the bone dry absorbent composite. The composite is softened as set forth in Example 5 and is found to have an average shakeout value of about 0.04 percent, a basis weight of 154 grams per square meter and a density of 0.14 grams per cubic centimeter.

COMPARATIVE EXAMPLE 1

A laminate structure according to the prior art is formed. The laminate is formed from a wet-laid fiber sheet formed from 78 weight percent superior bleached softwood pulp and 22 weight percent of a bleached cedar pulp. The fiber sheet is formed according to methods known to those skilled in the art and has a basis weight of 45 grams per square meter. The laminate is formed by spraying a bottom fiber sheet with water to a 60 percent pick-up and applying a 75 grams per square meter layer of absorbent material, which absorbent material is then covered with a second fiber sheet identical to the first. The laminate structure comprising about 45 weight percent absorbent material and about 55 weight percent fibers is then compressed in a rubber/steel nip and dried over steam cans. The absorbent material comprises a polyacrylate resin commercially available from Stockhausen under the designation Favor-840. The laminate is found to have an average shakeout value of about 0.07 percent, a basis weight of about 165 grams per square meter and a density of about 0.33 grams per cubic centimeter. FIG. 2 is a cross sectional scanning electron photomicrograph of this laminate material.

COMPARATIVE EXAMPLE 2

A laminate structure according to the prior art is formed. The laminate is the same as that of Comparative Example 1 with the exception that instead of using 75 grams per square meter of absorbent material, 290 grams per square meter of absorbent material is used. Also, the laminate is dried under compression on a laboratory steam can. The laminate is found to have an average shakeout value of about 1.6 percent, a basis weight of about 185 grams per square meter and a density of about 0.33 grams per cubic centimeter.

COMPARATIVE EXAMPLE 3

A commercially available laminate is purchased from Gelok International Corporation. The laminate consists of two 48 grams per square meter air-formed pulp sheets and a 75 grams per square meter layer of absorbent material. The absorbent material is the same as that employed in Comparative Example 1. The air-formed pulp sheets are spray bonded with an ethylene vinyl acrylate bonding agent. The laminate is found to have an average shakeout value of about 0.02 percent, a basis weight of about 396 grams per square meter and a density of about 0.32 grams per cubic centimeter. A cross sectional scanning electron photomicrograph of this material appears as FIG. 3.

As can be seen from reference to FIGS. 10–12, the absorbent material can be positioned in various locations within the wet-formed composites of the present invention. This may be advantageous in affecting the absorbent properties, fluid transport, and physical and mechanical properties of the composites. Also, by comparison of the shakeout values reported for Examples 4–6 and Comparative Examples 1 and 2, it is seen that the wet-formed composites of the present invention are superior in containing absorbent material. This improvement is particularly clear at higher concentrations of absorbent material.

It is to be understood that many modifications and variations of the described process and composite will be apparent to those skilled in the art. All such variations are intended to be within the scope of the present invention. It is to be further understood that the invention is not to be limited to the specific construction, arrangements and devices shown and described, as multiple changes may be made without departing from the principles of the present invention.

What is claimed is:

1. A method for the manufacture of a wet-formed composite, said method comprising the following steps:

forming a slurry of fibers and a dispersion medium from which slurry a wet-formed composite can be made;

combining an absorbent material, swellable in said dispersion medium, with said slurry of fibers immediately prior to forming a wet-formed composite wherein said absorbent material is in the form of a dry particle;

forming a wet-formed composite containing a combination of fiber and absorbent material; and drying said wet-formed composite.

2. The method according to claim 1 wherein said dispersion medium comprises water.

3. The method according to claim 1 wherein the fiber comprises cellulosic fibers.

4. The method according to claim 1 wherein said absorbent material and said slurry of fibers are combined in a headbox.

5. The method according to claim 1 further comprising the step of partially swelling the absorbent material in said dispersion medium prior to forming said wet-formed composite.

6. The method according to claim 5 wherein the absorbent material absorbs less than about 5 times its weight in said dispersion medium prior to the drying of said wet-formed composite.

7. The method according to claim 1 wherein said absorbent material and said slurry of fibers are generally uniformly mixed.

8. The method according to claim 4 wherein said headbox is a multiple-flow channeled headbox.

9. The method according to claim 1 further comprising the step of dewatering said wet-formed composite through application of vacuum immediately after formation of said wet-formed composite.

10. A method for the manufacture of a wet-formed composite, said method comprising the following steps:

forming a slurry of fibers and a dispersion medium from which slurry a wet-formed composite can be made;

combining an absorbent material, swellable in said dispersion medium, with said slurry of fibers such that said absorbent material absorbs less than about 10 times its weight in said dispersion medium prior to forming said wet-formed composite wherein said absorbent material is in the form of a dry particle;

forming a wet-formed composite containing a combination of fiber and absorbent material; and drying said wet-formed composite.

* * * * *